United States Patent [19]
Macartney et al.

[11] Patent Number: 5,306,270
[45] Date of Patent: Apr. 26, 1994

[54] SEALING CLOSURE CAP AND BIOLOGICAL SAMPLE COLLECTION TUBE

[75] Inventors: Charles T. Macartney, Georgetown; Victor A. Daykin, Pickering, both of Canada

[73] Assignee: Starplex Scientific, Etobicoke, Canada

[21] Appl. No.: 636,317

[22] Filed: Dec. 31, 1990

Related U.S. Application Data

[63] Continuation-in-part of Ser. No. 486,550, Feb. 28, 1990, abandoned.

[51] Int. Cl.$^5$ ............................................. A61J 1/00
[52] U.S. Cl. .................................. 604/415; 604/403; 128/760
[58] Field of Search ................ 604/403, 411-416; 128/760, 765; 215/355, 33, 247

[56] References Cited

U.S. PATENT DOCUMENTS

| | | | |
|---|---|---|---|
| 3,105,613 | 10/1963 | Barton et al. ................ | 604/415 X |
| 4,089,432 | 5/1978 | Crankshaw et al. ........... | 215/406 |
| 4,227,620 | 10/1980 | Conway ........................ | 215/355 |
| 4,373,009 | 2/1983 | Winn ............................ | 604/280 |
| 4,465,200 | 8/1984 | Percarpio ..................... | 604/415 |
| 4,477,578 | 10/1984 | Miles et al. . | |
| 4,624,664 | 11/1986 | Peluso et al. ................. | 604/256 |
| 4,657,151 | 4/1987 | Cabernoch . | |
| 4,856,533 | 8/1989 | Anraku et al. ................ | 128/763 |
| 4,902,521 | 2/1990 | Rosenfeld . | |
| 4,985,026 | 1/1991 | Kasai et al. .................. | 604/403 |
| 5,061,263 | 10/1991 | Yamazaki et al. ............. | 604/403 |
| 5,066,209 | 11/1991 | Schmaderer et al. . | |

OTHER PUBLICATIONS

Fisher Scientific, catalogue 88, pp. 1506–1509 and 1512–1513 dated 1988.
Wheaton Catalogue, pp. 66 dated 1989.

*Primary Examiner*—Robert A. Hafer
*Assistant Examiner*—Sam Rimell

[57] ABSTRACT

A biological sample collection tube suitable for use in collecting and processing blood samples, is of high strength, transparent plastic. The tube wall is substantially gas impermeable, permitting the retention of samples therein, under conditions of vacuum, for prolonged periods. The selected material is combustible in air, yielding products of combustion that are substantially non-toxic, to facilitate the safe disposal of the tubes, together with the enclosed samples. The tube is made of plastic copolymer or monomer resin such as polyethylene, polypropylene or polyamide. A preferred material group is amorphous nylon, in particular Nylon 6 (T.M.) such as polyethylenenaphthalate and ethylene vinyl alcohol. The tube may be made from a combination of such materials by mechanical integration in manufacture, through co-extrusion, co-injection, or by a dual material indexed molding process. The impermeability of the tube wall may be enhanced by the application of a sealing coating of polyvinyldichloride, applied to the inner and/or the outer surface of the tube wall. The tube is compatible with a wide range of inner wall coating substances, to facilitate the processing of blood samples. A sealing cap for use with the improved tube has a tapered or parallel body of a thermoplastic elastomer, one embodiment of which incorporates a safety overcap to limit the formation of an aerosol when the tube is opened.

1 Claim, 1 Drawing Sheet

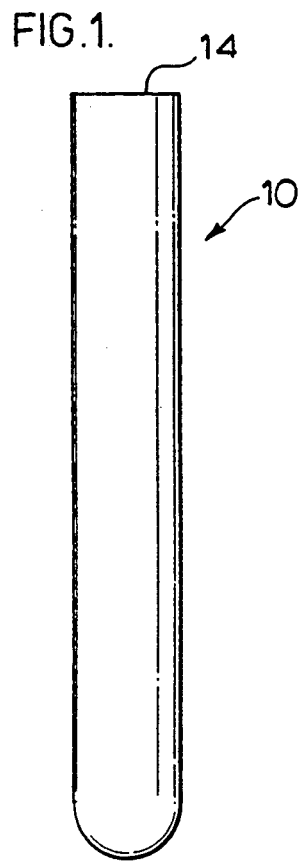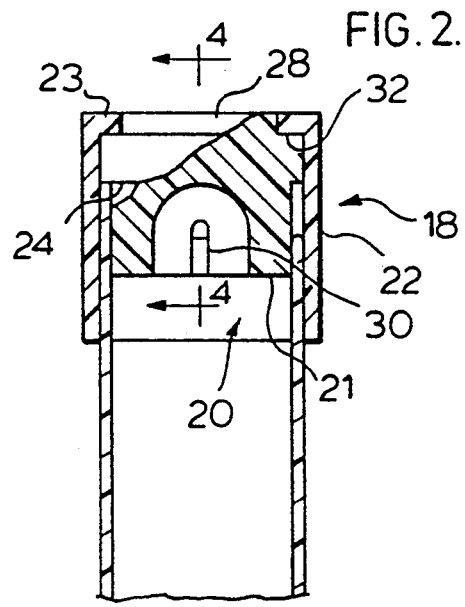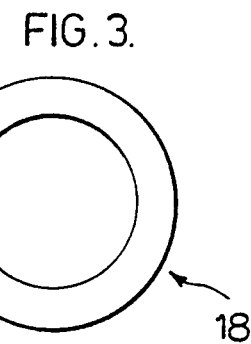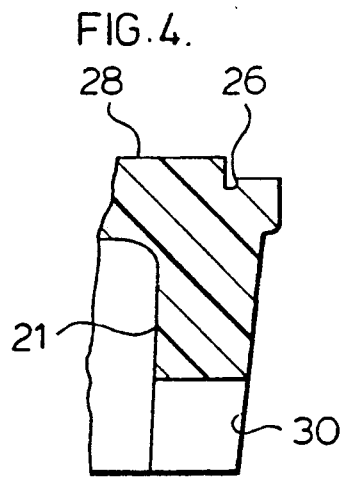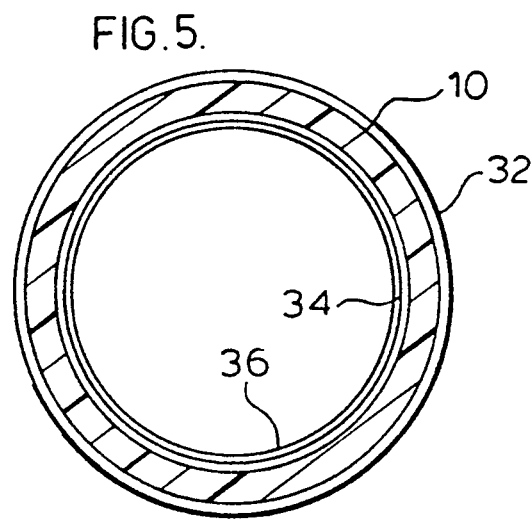

SEALING CLOSURE CAP AND BIOLOGICAL SAMPLE COLLECTION TUBE

This application is a continuation-in-part of application Ser. No. 07/486,550, filed Feb. 28, 1990, now abandoned.

FIELD OF THE INVENTION

This invention is directed to a sample container, and in particular to a sample tube suitable for use with blood samples, and biological or chemical samples.

BACKGROUND TO THE INVENTION

The traditional tube used in the collection and processing of biological samples has been the glass test tube, and variations thereof.

The brittleness of glass, together with its general weakness, a tendency to shatter, and to form dangerous cutting surfaces when broken, as well as its non combustibility have militated against its use.

These disadvantages of glass are particularly emphasized in relation to the handling of blood samples wherein a retro-virus such as HIV-manifesting or the AIDS virus, or other infectious or hazardous substances may be present.

Thus, the use of a potentially shatterable tube for collection and transportation of potentially highly infectious and hazardous substances is evidently undesirable, while the sharpness of its shards with their inherent capacity to wound and infect makes continuing use thereof untenable.

The adoption of plastic tubes for purposes of blood separation, by way of coagulation, and separation of serum by centrifugal separation is taught by U.S. Pat. No. 4,856,533 granted Aug. 15th, 1989.

In the case of tubes for use in blood analysis work a group of surface active coatings exists including, Ethylenediaminetetraacetate (E.D.T.A.), finely divided silica gel, silica, sodium heparin, silicon and its modifications, potassium oxalate, sodium chloride, sodium citrate, citric acid, kaolin.

However, the gas sealing capability of these materials is quite limited, when considered in relation to glass, as an illustrative standard. Furthermore, particularly in the case of acrylonotrile group of resins, these are peculiarly inappropriate for the proposed usage as they form cyanide gas when incinerated, and are thus unsuited to incineration.

The need to provide safe incineration when disposing of blood samples possible containing the AIDS virus or infectious substances together with the contaminated tube, evidently requires no argument.

The above-identified document teaches also the need for the use of a hydrophilic surface coating on the interior of the collection tube, to preclude adhesion of a blood clot to the tube walls due to the existence of an undue number of blood coagulation sites on the plastic surface.

Use of inorganic adsorptive substances such as glass, silica, kaolin, cerite etc., is combined with a water soluble substance and an adsorptive inorganic substance to achieve coagulation in a controlled fashion. The examples taught comprise modified aliphatic silicone oils, modified aromatic silicone oils, modified paraffin, modified wax, etc., for which a number of examples are given.

Examples of water soluble substances that are given comprise low molecular weight and high molecular weight substances, particularly intended for blood fraction separation.

SUMMARY OF THE INVENTION

In accordance with the present invention there is provided a strong, lightweight biological sample collection vessel comprising a substantially tubular vessel of predetermined size, having an opening for the passage of the sample and associated fluids therethrough, the wall of the vessel being of transparent plastic substantially impermeable to the passage of air therethrough, and providing substantially nontoxic products of combustion when incinerated.

In a preferred embodiment the tube of the present invention is made of plastic copolymer of monomer resin such as polyethylene, or polypropylene, or polyamide, such as amorphous nylon, and in particular a Nylon 6 (T.M.) such as polyethylenenaphthalate, or ethylene vinyl alcohol. The tube may comprise any of the individual resins or it may be made as a mechanically integrated combination thereof from a combination of the above-identified materials through co-extrusion; by co-injection; or by a dual material indexed molding process. The impermeability of the tube may be enhanced by a sealing coating of polyvinyldichloride applied to the inner and/or outer surface thereof.

Advantages provided by the above-identified tubes in accordance with the present invention include enhanced air separation (i.e. vacuum maintenance), high strength and shatter resistance.

A tube made of these plastic materials (in particular Amorphous Nylon) possesses a highly desirable surface structure characteristics, in regard to blood clotting activity, without the presence of undesired coagulation sites, and without requiring the use of any special clot activators, which favorable characteristics enable the achieving of greatly accelerated clotting-times (as low as ten minutes), which existing products may not achieve.

In a further embodiment there is provided a safety sealing plug or cap for use with a plastic sample collection tube, the cap having a tapered resilient sealing plug portion for insertion axially in sealing relation within the mouth of the tube; and an annular skirt surrounding the plug portion in radially spaced relation therefrom, the skirt extending axially beyond the plug portion, in use to provide an air flow control passage between the skirt and the tube upon withdrawal of the tapered plug portion from the tube mouth.

The crown portion of the plug is injection molded from thermoplastic elastomer (TPE) of predetermined Shore durometer range, to permit the insertion or withdrawal therethrough of a hollow needle or cannula, in intact sealing relation therewith. Upon withdrawal of the needle or cannula, the plug is substantially unimpaired in its sealing capability.

A preferred embodiment provides a slotted closure plug wherein a skirt portion of the plug is-perforated by a slot, for a portion of its length adjoining its lower edge, to control air ingress and egress during plug displacement.

In a further embodiment the annular skirt is fluted so as to provide, in use a series of axially extending parallel air access passages, together with an attachment surface of enhanced characteristics. The radially inner surfaces of the fluted portion may contact the adjacent outer surface of the tube.

In operation, on closure of the cap there is provided an air flow passage, to facilitate displacement of the tube into and from the annular space extending between the cap plug and the cap skirt.

However, it is on opening of the tube by removal of the plug that the air flow control function plays its most important role, wherein the restricted air flow passages provided serve to control the ingress of air to the tube as the plug is withdrawn from the mouth of the tube, so that the tendency to generate an aerosol mixture between the inflowing air and the contents of the tube, is effectively limited with correspondingly reduced propagation of the aerosol outside the tube.

It will be understood that the tube in accordance with the present invention may utilize caps ranging from a simple elastomeric stopper to more complex arrangements.

The use of a threaded tube and screw cap also is contemplated.

BRIEF DESCRIPTION OF THE DRAWINGS

Certain embodiments of the invention are described by way of illustration, without limitation of the invention thereto, reference being made to the accompanying drawings, wherein:

FIG. 1 is a side view of a collection tube in accordance with the present invention;

FIG. 2 is a diametrical cross section of a portion of the subject collection tube in partially assembled relation with a plug cap according to the invention;

FIG. 3 is a plan view of the cap of FIG. 2;

FIG. 4 is a portion of an enlarged section, taken at 4—4 of FIG. 3; and

FIG. 5 is a composite section showing tube coating arrangement.

DETAILED DESCRIPTION OF THE INVENTION

Referring to the drawings, a tube 10 has a slight taper in the length thereof, having an open mouth 14, and is of substantially uniform wall thickness.

A plug cap 18 has a tapered resilient sealing plug portion 20 and an outer skirt portion 22 extending from a crown portion 23. The plug portion 20 has an annular tongue portion 21 and an enlarged head portion 24, with an annular groove 26 recessed therein, surrounding on upstanding spigot portion 28. A transverse groove 30, see FIGS. 2 and 4 extends through the tongue portion 21, adjoining the insertion end thereof.

The outer skirt portion 22 of plug cap 18 has an axially extending internal annular spigot 32 which engages the groove 26 of plug portion 24, when the component parts of plug cap 18 are assembled.

In use, when the plug cap 18 is removed from a tube 10 that contains fluid contents, such as a blood sample, the initial displacement of plug cap 18 to the position shown in FIG. 2 positions the inner end of groove 30 above the upper edge of tube 10, thus providing a small aperture for the controlled passage of air therethrough. The rate of pressure equalization is further controlled by the axial overlap of skirt 22 with the tube 10. This controlled pressure equalization substantially precludes the formation and projection of an aerosol, formed from the fluid contents of tube 10.

The annular tongue portion 21 of plug cap 18 is of predetermined thickness and durometer value to assure effective sealing of the tube 10 for a duration of many months. The injection molded crown portion 28 permits the piercing thereof by a cannula or needle and retention therein in sealed relation, with re-establishment of the sealing function of the pierced crown 28 upon withdrawal of the cannula or needle. A dynamically vulcanized butyl rubber cross linked to polypropylene, in the durometer range Shore A 40 to 60 is suitable for this purpose, such as Monsanto TPE 3281-55 (T.M.).

The outer skirt portion of plug cap 18 is of polyethylene or polypropylene. The plug portion 20 generally is thermo-mechanically bonded thereto, by way of the upper surfaces of head portion 24.

Referring to the FIG. 5 embodiment, the tube 10 is illustrated as having both an exterior and an interior barrier coating 32, 34. In general, only one such barrier layer would be applied, to either the inner of the outer major surface area of the tube. The preferred barrier layer, 32, 34 is polyvinyldichloride (PVDC), applied in adherent sealing relation to at least one, inner or outer, major surface area of the tube.

The interior layer 36, used as an interior surface coating for blood analysis work to facilitate coagulation may comprise one of the above listed surface active coatings such as EDTA, finely divided silica gel, silica, silicone, sodium heparin, lithium heparin, thymol, ammonium heparin, potassium oxylate, water and sodium chloride, sodium fluoride, sodium citrate and citric acid.

The embodiments of the invention in which an exclusive property or privilege is claimed are defined as follows:

1. A safety plug for use with a tube, in inserted, sealing relation therewith, said plug having a central tapered resilient sealing annular tongue portion for insertion axially in sealing relation within the mouth of said tube; said plug having a lateral passage therethrough of predetermined size, connecting the interior of said annular tongue portion to a space within said annular skirt to provide in use a controlled access to said tube, on displacement of said passage past the rim of said tube, said plug portion being of thermoplastic elastomer, having a predetermined durometer to permit penetration and resealing closure of a cannula and an axially extending outer annular skirt bonded thereto and projecting downwardly below said tongue portion, in use, upon withdrawal of said tongue portion in separating relation above the rim of said tube to provide an air flow passage between said tube interior and said extended skirt interior, to control the rate of ingress of air to the tube.

* * * * *